United States Patent
Morita et al.

(10) Patent No.: US 6,875,230 B1
(45) Date of Patent: Apr. 5, 2005

(54) MECHANICAL HEART VALVE AND PRODUCTION METHOD THEREOF

(75) Inventors: Shinichiro Morita, Ayabe (JP); Saburo Nakamura, Ayabe (JP); Shigeyuki Hirata, Moriyama (JP); Toshiharu Shin'oka, Tokyo (JP); Yasuharu Imai, Tokyo (JP)

(73) Assignees: Gunze Limited, Kyoto (JP); Tokyo Women's Medical University, Tokyo (JP)

( * ) Notice: Subject to any disclaimer, the term of this patent is extended or adjusted under 35 U.S.C. 154(b) by 0 days.

(21) Appl. No.: 10/111,244

(22) PCT Filed: Oct. 19, 2000

(86) PCT No.: PCT/JP00/07265

§ 371 (c)(1),
(2), (4) Date: Apr. 19, 2002

(87) PCT Pub. No.: WO01/30274

PCT Pub. Date: May 3, 2001

(30) Foreign Application Priority Data

Oct. 22, 1999 (JP) .................................. 11-301632

(51) Int. Cl.[7] .............................................. A61F 2/24

(52) U.S. Cl. .................................... 623/2.12; 623/2.42

(58) Field of Search .......................... 623/2.12, 2.13, 623/2.14, 2.15, 2.16, 2.17, 2.18, 2.19, 2.42

(56) References Cited

U.S. PATENT DOCUMENTS

| 4,192,020 A |   | 3/1980  | Davis et al. |
| 4,364,127 A |   | 12/1982 | Pierce et al. |
| 4,510,628 A | * | 4/1985  | Kolff ......................... 623/2.19 |
| 4,728,328 A |   | 3/1988  | Hughes et al. |
| 4,916,193 A |   | 4/1990  | Tang et al. |
| 5,011,494 A |   | 4/1991  | von Recum et al. ...... 623/23.74 |
| 5,139,515 A |   | 8/1992  | Robicsek |
| 5,290,494 A |   | 3/1994  | Coombes et al. |
| 5,489,297 A |   | 2/1996  | Duran ........................ 623/2.13 |
| 5,527,337 A | * | 6/1996  | Stack et al. ................. 606/198 |
| 5,545,215 A |   | 8/1996  | Duran |
| 5,700,286 A | * | 12/1997 | Tartaglia et al. ........... 623/1.15 |
| 5,855,610 A |   | 1/1999  | Vacanti et al. |
| 6,364,905 B1 | * | 4/2002 | Simpson et al. .......... 623/2.13 |

FOREIGN PATENT DOCUMENTS

| EP | 0 744 162 A3 | 12/1997 |
| JP | 11-503051 | 3/1999 |
| WO | WO 90/02796 | 3/1990 |
| WO | WO 96/08213 | 3/1996 |
| WO | WO 96/31157 A1 | 10/1996 |
| WO | WO 99/11297 A2 | 3/1999 |
| WO | WO 99/47188 A1 | 9/1999 |

\* cited by examiner

*Primary Examiner*—Corrine McDermott
*Assistant Examiner*—Thomas J Sweet
(74) *Attorney, Agent, or Firm*—Knobbe, Martens Olsen & Bear LLP

(57) ABSTRACT

An artificial heart valve comprising a tubular base body having sinuse(s) of Valsalva and valve cusp(s) provided inside the base body, characterized in that the base body and the valve cusps comprise a bioabsorbable polymer material.

11 Claims, 4 Drawing Sheets

MECHANICAL HEART VALVE AND PRODUCTION METHOD THEREOF

TECHNICAL FIELD

The present invention relates to an artificial heart valve and production method thereof.

BACKGROUND ART

As observed in mitral stenosis, mitral insufficiency (regurgitation), aortic stenosis, aortic insufficiency, tricuspid insufficiency and like valvular heart diseases, when a heart valve does not properly function and stenosis or regurgitation occurs, the heart valve must be replaced. There are three kinds of heart valves which are currently used in heart transplant operations: (1) mechanical valves, (2) heterograft valves and (3) homograft valves.

Mechanical valves have excellent durability; however, they require recipients to take an anticoagulant throughout their lifetime. Heterograft valves, which use valves from animals, do not require recipients to take an anticoagulant throughout their lifetime; however, the valves tend to malfunction after 6 to 10 years. Alternatively, frozen homograft valves harvested from cadavers exhibit more favorable long term results than heterograft valves. Therefore, the frozen homograft valves are widely used in Europe and America where use of cadaver tissue is advanced; however, the drawback of short supply exists.

A method for regenerating various kinds of tissues in a living body by employing tissue engineering techniques has recently been developed, wherein cells of autogenous tissue are seeded and cultured on a scaffold made of a bioabsorbable polymer so as to regenerate the autogenous tissues. Quite a few research reports have been published on the tissue regeneration method applied to skin regeneration (M. L. Cooper, L. F. Hansbrough, R. L. Spielvogel et al. "In vivo optimization of a living dermal substitute employing cultured human fibroblasts on a biodegradable polyglycolic acid or polyglactin mesh." *Biomaterials* 12 (1991): 243–248) and cartilage regeneration (C. A. Vacanti, R. Langer et al. "Synthetic polymers seeded with chondrocytes provide a template for new cartilage formation." *Plast. Reconstr. Surg.* 88 (1991): 753–759).

Regeneration of heart valves has also been tested using tissue engineering techniques and a study regarding regeneration of heart valve leaflets has reported good results (T. Shin'oka et. al. "Tissue-engineered heart valve leaflets. Autologous valve leaflet replacement study in a lamb model." *Circulation* 94 (suppl. II) (1996): II-164-II-168. T. Shin'oka et al. "Tissue-engineered heart valve leaflets. Does cell origin affect outcome?" *Circulation* 96 (suppl. II) (1996): II-102-II-107).

However, practically usable bioabsorbable substrates which enable the entire heart valve to be made of bioabsorbable material have not yet been developed.

An object of the present invention is to provide a practically usable bioabsorbable substrate which enables the entire heart valve to be made of bioabsorbable material.

DISCLOSURE OF INVENTION

Figure 1:
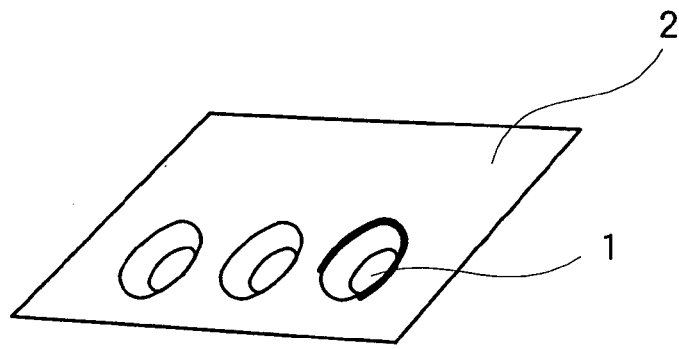
FIG. 1 is an extend elevation showing a tubular structure having sinuses of Valsalva.

The present invention relates to the artificial heart valves and production methods thereof described below.

Item 1. An artificial heart valve comprising a tubular base body having sinus(es) of Valsalva and valve cusps provided inside the base body, characterized in that the base body and the valve cusp(s) comprise a bioabsorbable polymer material.

Item 2. The artificial heart valve according to item 1, wherein the bioabsorbable polymer material used as a material for the base body and/or the valve cusp(s) contains a reinforcement having a fibrous structure made of a bioabsorbable polymer.

Item 3. The artificial heart valve according to item 1, wherein the base body and/or the valve cusp(s) are porous.

Item 4. An artificial heart valve formed by seeding living cells into the artificial heart valve according to any one of items 1 to 3.

Item 5. A process for producing an artificial heart valve comprising the steps of forming sinus(es) of Valsalva on a base body and combining valve cusp(s) with the base body.

Item 6. The process according to item 5, wherein the combining of the valve cusp(s) with the base body is conducted by adhesion.

Item 7. The process according to item 5, wherein the combining of the valve cusp(s) with the base body is conducted by suture.

Item 8. The process according to item 7, wherein the suture is conducted using a bioabsorbable suture.

Item 9. The process according to item 5, wherein the combining of the valve cusp(s) with the base body is conducted by thermal fusion.

Item 10. The process according to item 5, wherein the combining of the valve cusp(s) with the base body is conducted by using a bioabsorbable polymer solution.

Item 11. The process according to item 5, wherein the tubular base body having sinus(es) of Valsalva is formed by molding and one end of a substrate is folded and subjected to heat set so as to form the valve cusp(s).

Examples of bioabsorbable materials include polyglycolic acid, polylactic acid (D form, L form, DL form), polycaprolactone, glycolic acid-lactic acid (D form, L form, DL form) copolymer, glycolic acid-caprolactone copolymer, lactic acid (D form, L form, DL form)— caprolactone copolymer, poly(p-dioxanone) and like synthetic bioabsorbable polymers, collagen, denatured collagen, gelatin, chitin, chitosan and like natural polymers, etc.

The artificial heart valve of the invention comprises a sponge made of bioabsorbable material(s), film, nonwoven fabric and the like. When the artificial heart valve of the invention must have a certain level of strength, it can be reinforced by a reinforcement comprising fabric, textile, nonwoven fabric or the like which is also made of a bioabsorbable polymer.

The reinforcement and the body of the artificial heart valve may use the same or different bioabsorbable materials.

For preparation of the heart valve, the following alternative processes, among others, are available.

(1) Production of Valsalva Sinus

A base body having sinus(es) of Valsalva can be obtained by pouring a bioabsorbable polymer solution into a mold designed for a base body having a Valsalva sinus structure, freezing and then lyophilizing. The mold can be flat or hollow cylindrical (doughnut-shaped). When the mold for the base body is flat, the obtained sheet-shaped base body can be made tubular by suture, thermal fusion or the like.

A base body having a reinforcement can be obtained by following the production steps of setting the fabric, textile, nonwoven fabric or like reinforcement made of a bioabsorbable polymer in the outer mold for the base body having sinus(es) of Valsalva, pouring a bioabsorbable polymer solution into the cavity, freezing and then lyophilizing. The thus obtained base body is porous.

(2) Production of Valve Cusps (Inner Valve)

Figure 2:
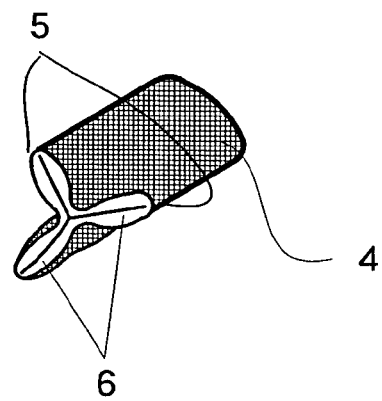
FIG. 2 shows a tricuspid valve.
Figure 3:
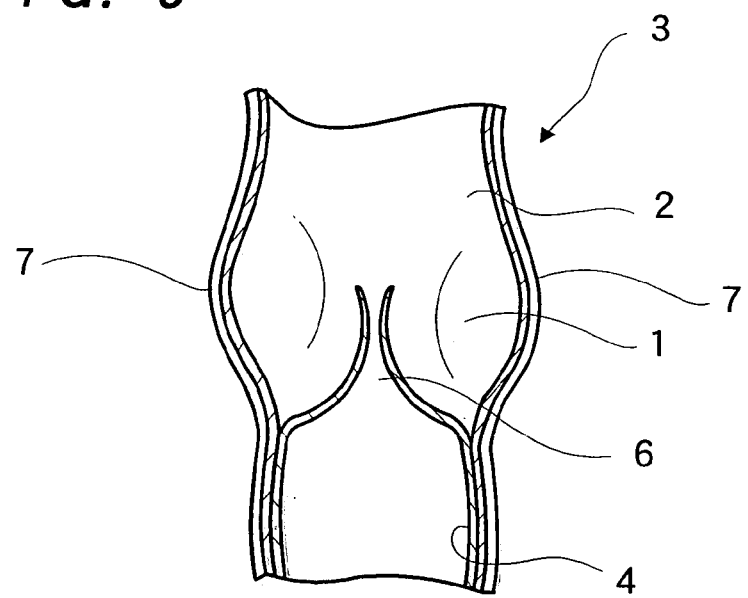
FIG. 3 is a cross-sectional view of an artificial heart valve of the invention.
Figure 4:
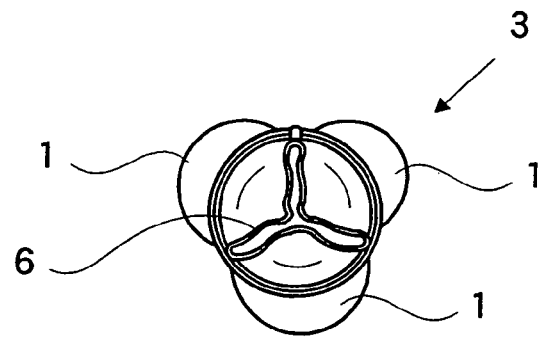
FIG. 4 is a plan view of an artificial heart valve of the invention.
Figure 5:
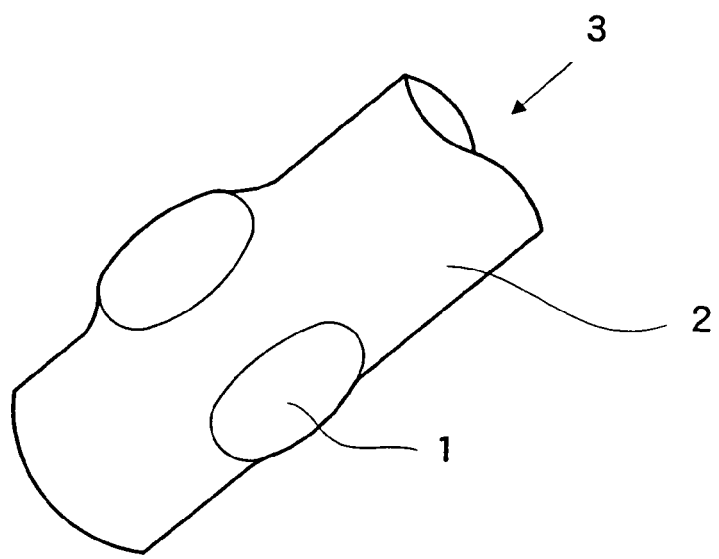
FIG. 5 is a perspective view of an artificial heart valve of the invention.

A tubular fabric or textile or a flat fabric or textile is wrapped around a Teflon test tube. The fabric or textile is fused or sutured into a tubular shape. Then, this assembly is set in an outer mold. Thereafter, a bioabsorbable polymer solution forming a substrate is poured into the cavity, frozen and then lyophilized. Thus, a porous tubular substrate can be obtained. The tubular substrate is removed from the mold, one of the ends thereof is folded in such a manner that the inner sides thereof attach to each other (in the case of a bicuspid valve, from two directions; and in the case of a tricuspid valve, from three directions), and then the substrate is heat set to obtain valve cusps (FIG. 2).

(3) Combination

A valve cusp is inserted around the position of the Valsalva sinus in a tubular base body constructed as above. Then, the non-folded end of the valve cusp is sutured to the tubular base body in the vicinity of the Valsalva sinus with a bioabsorbable suture. The thus obtained heart valve substrate is used in the following Examples after being subjected to gas sterilization by ethylene oxide.

(4) Culture and Seeding of Cells

Living cells (endothelial cells, fibroblasts, smooth muscle cells and the like) are collected from femoral arteries, grown in mixed-culture and seeded in the artificial heart valve in such a manner that they become endothelial cells.

(5) Implantation

The thus produced heart valve can be implanted in the body of an adult or animal, and is advantageously usable for implantation into an infant or child.

The invention provides an artificial heart valve usable in lieu of mechanical, heterograft and homograft heart valves.

Because the artificial heart valve of the invention comprises a bioabsorbable polymer material, it does not remain in vivo as a foreign substance after the tissue has regenerated. When implanted into an infant, it can keep pace with the infant's growth. Furthermore, the porous structure provides excellent adhesiveness for cells.

BEST MODE FOR CARRYING OUT THE INVENTION

The following example is further illustrative of the present invention.

EXAMPLE 1

(1) Production of Tubular Structure

Figure 7:
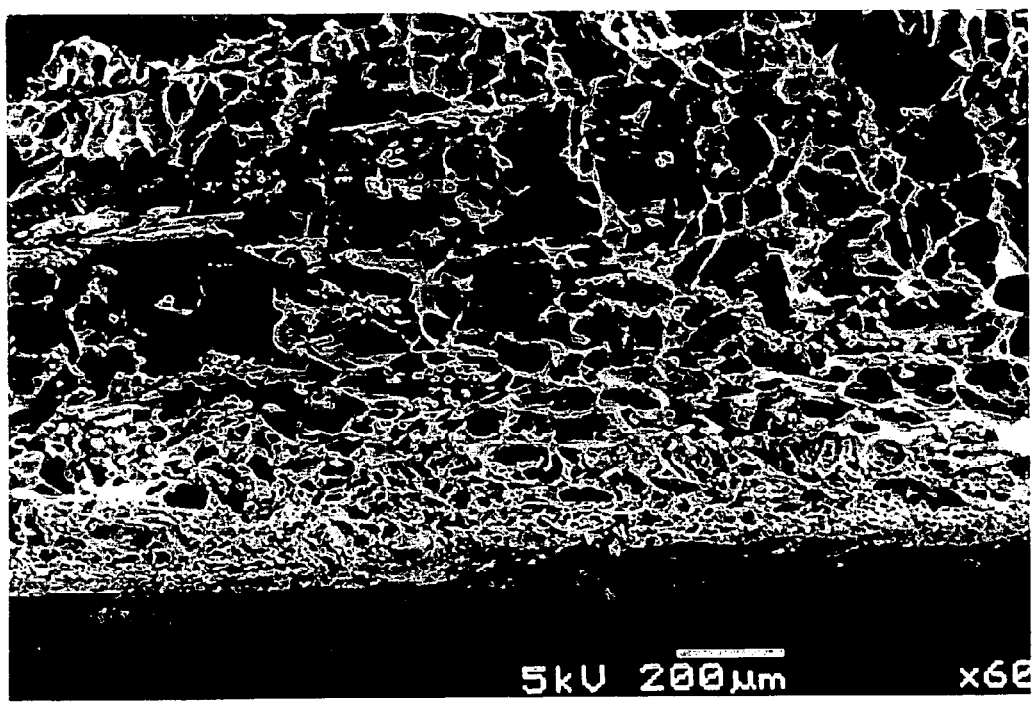
FIG. 7 is a photograph showing a cross-sectional view of the tubular structure.
Figure 8:
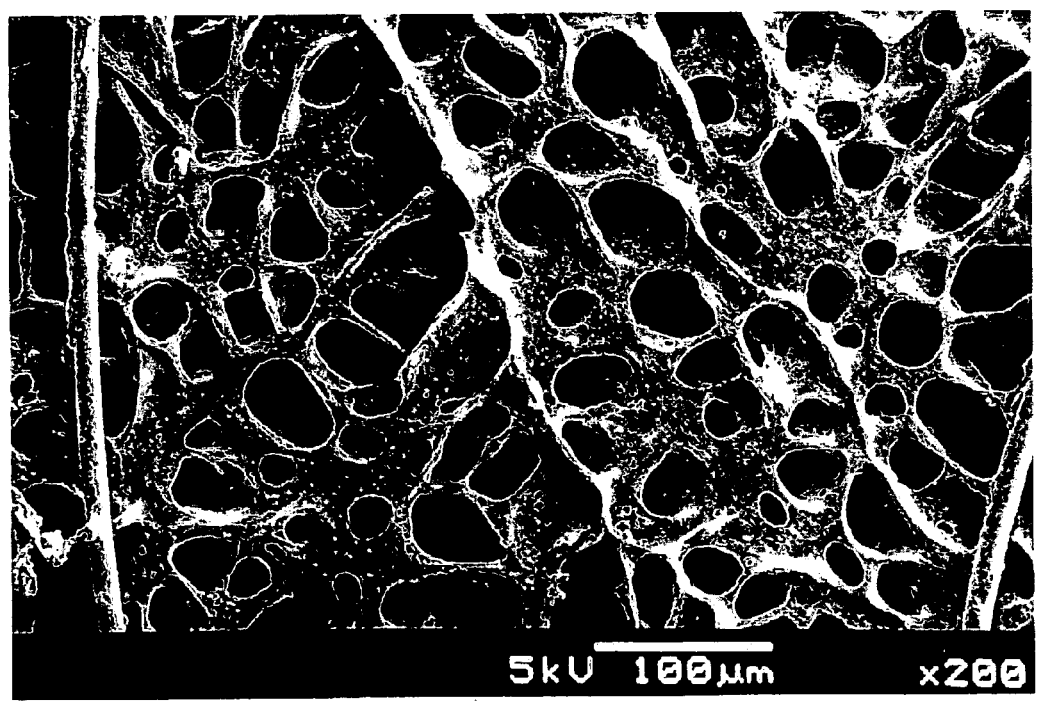
FIG. 8 is a photograph showing a plan view of the tubular structure.

A tubular textile made of polyglycolic acid was set in a mold (20 mm in diameter) designed for a tubular structure having a Valsalva sinus structure 1. The inner mold was put into place from the inside, then a solution of lactic acid-caprolactone copolymer (molar ratio 50:50) in dioxane (5%) was poured into the cavity, frozen at -30° C. and lyophilized at 20° C. for 24 hours. The base body 2 obtained after lyophilization was tubular having a cellular substrate reinforced with a fibrous material in the center (FIG. 7 shows a photograph of a cross-sectional view and FIG. 8 shows a photograph of a plan view). FIG. 1 is an extend elevation showing the tubular structure.

(2) Production of Valve Cusps

Figure 9:
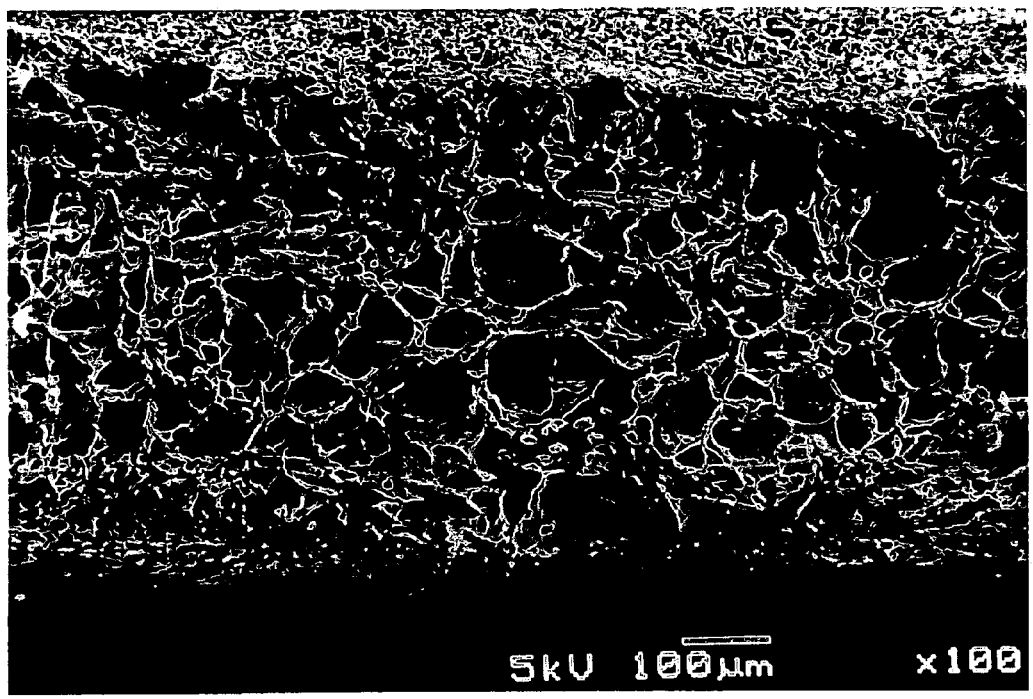
FIG. 9 is a photograph showing a cross-sectional view of a tubular used for forming a valve cusp.
Figure 10:
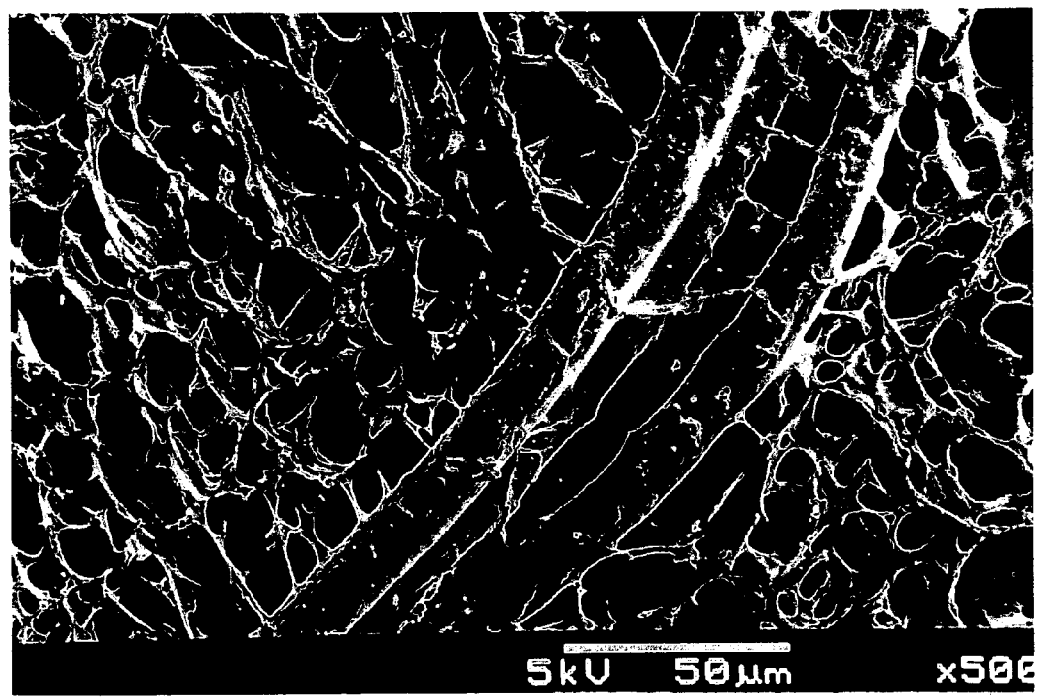
FIG. 10 is a photograph showing a plan view of tubular substrate used for forming a valve cusp.

A tubular textile made of polyglycolic acid was wrapped around a Teflon test tube having a diameter of 18 mm. This assembly was set in a tubular mold having a diameter of 20 mm, then a solution of lactic acid-caprolactone copolymer (molar ratio 50:50) in dioxane (5%) was poured into the cavity, frozen at -30° C. and lyophilized at 20° C. for 24 hours. The thus obtained valve cusps had a cellular substrate reinforced with a fibrous material in the center (FIG. 9 shows a photograph of a cross-sectional view and FIG. 10 shows a photograph of a plan view). The tricuspid valve 4 as shown in FIG. 2 was obtained by folding the end thereof from three directions, suturing the folded areas together in the center, subjecting them to heat set at 100° C. under vacuum for three hours. After completion of the heat set, the suture was cut.

Figure 6:
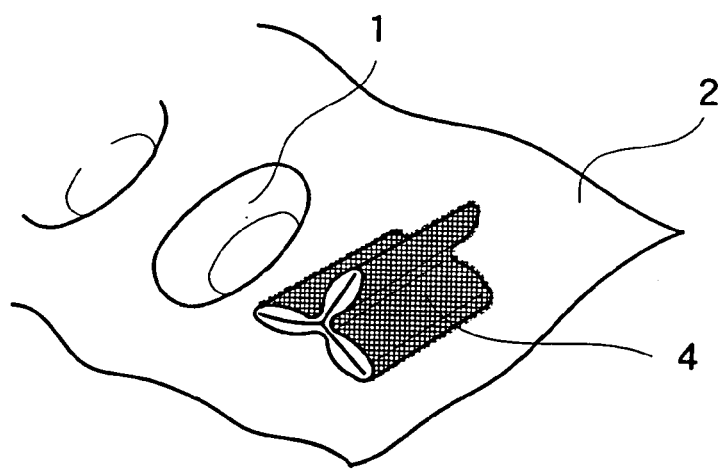
FIG. 6 shows a tricuspid valve 4 integrally sutured with sinuses of Valsalva 1 on a sheet-shaped base body 2.

Combination could also be conducted using the sheet-shaped base body 2 shown in FIG. 6, and forming it into tubular form after integrally suturing the Valsalva sinus 1 and the tricuspid valve 4 as described earlier.

(3) Combination

A valve cusp 4 was set in a tubular structure having a Valsalva sinus structure 1, each apex 5 of the tricuspid valve 4 was integrally sutured with the periphery of Valsalva sinus 1 by polyglycolic acid suture, and then the other end of the tricuspid valve 4 and the base body were integrally sutured in a tubular form, obtaining the artificial heart valve 3 of the invention containing the valve 6.

(4) Cell Culture

A. Cell Isolation, Culture, and Propagation

About 2 cm of femoral artery was collected from a 20-day-old Dover lamb under general anesthesia while preserving the deep femoral artery intact. The tissue, which was isolated in a sterile environment, was immersed in a cell culture medium and washed with phosphate-buffered saline in a clean bench. Then, on a petri dish, the tissue was cut into pieces using a surgical knife according to the simple explant technique. Tissue pieces sized about 1–2 mm were distributed uniformly on the dish and after about 20 minutes, when the tissue pieces intimately adhered to the bottom of the dish, a culture medium was added. This step was carefully conducted so as not to peel off the tissue pieces.

As the culture medium, Dulbecco's Modified Eagles Medium (DMEM) supplemented with 10% fetal bovine serum and 1% antibiotic solution (L-glutamine 29.2 mg/ml, penicillin G sodium 1000 U/ml, and streptomycin sulfate 10,000 µg/ml) was used.

The lamb vascular wall cells (mixed-cells) began to migrate from the tissue pieces on the dish after 5–7 days, forming mixed-cell colonies of endothelial cells, fibroblasts, and smooth muscle cells around the explants after one week. After another 2–3 weeks, the mixed-cells became confluent on the dish. Immediately, a passage was made using 0.25% trypsin and the culture in a 75 cm$^2$ culture flask was started. When the growth in this flask became confluent, about $2 \times 10^6$ cells were generally available. Cell culture was performed in an atmosphere comprising 5% of $CO_2$ and 95% of $O^2$ and continued until 10×10 cells were obtained. When the culture medium was renewed every 4–5 days, the doubling time of cells was about 48 hours.

B. Cell Sorting and Endothelial Cell Purification

At the stage when the mixed-cells became confluent and a reasonable number of cells was obtained, endothelial cells were sorted out from among the mixed-cells using FACS according to the following protocol. Dil-acetylated LDL (fluorescent marker; product of Biomedical Technologies) (briefly, Dil-Ac-LDL) was added to the mixed-cell culture at a concentration of 1 µg/ml, followed by 24-hour incubation. This marker was taken up intracellularly through a scavenger pathway specific to endothelial cells and macrophages. After 24 hours, the cells were trypsinized to prepare a mixed-cell suspension and sorting was performed using a cell sorter (FACS machine: product of Bectin Dickenson, Mountainview, Calif.). According to the size and emission of fluorescence, the cells were sorted into Dil-Ac-LDL-positive cells and Dil-Ac-LDL-negative cells. The endothelial cells, which are Dil-Ac-LDL-positive cells, represented about 5–8% of the mixed culture. After sorting, each type of cells was independently cultured until $2 \times 10^6$ endothelial cells were obtained. Incidentally, the counting of the cell population was carried out by the classical exclusion method using Trypan Blue.

C. Structure of Leaflets

The heart valve and a valve cusp substrate were seeded with about $2 \times 10^7$ Dil-Ac-LDL-negative myofibroblasts. Immediately following the seeding of a concentrated cell suspension on the matrix, the system was allowed to stand on the culture dish in a clean bench for 30–60 minutes, and thereafter about 50 ml of a culture medium was added. The culture medium was renewed every day as a rule and after 7 days, one day before implantation into an animal body, a further seeding was performed with a suspension of endothelial cells (about $2 \times 10^6$ cells), whereby a monolayer of endothelial cells was obtained.

D. Animal Experiment

A heart valve of a young dog was replaced with the heart valve constructed as above. A good patency was obtained without using an anticoagulant and it was verified that the heart valve of the invention was satisfactorily functioning as a tissue culture heart valve.

What is claimed is:

1. An artificial heart valve, comprising:
   a tubular base body having at least one sinus of Valsalva; and
   at least one valve cusp provided inside the base body, wherein both the sinus and the cusp are bioabsorbable, and at least one of the sinus or the cusp comprises a fibrous reinforcement structure made of a bioabsorbable polymer embedded in a porous bioabsorbable polymer material.

2. An artificial heart valve formed by seeding living cells into the artificial heart valve according to claim 1.

3. The artificial heart valve according to claim 1, wherein the bioabsorbable material is selected from the group consisting of polyglycolic acid, polylactic acid, polycaprolactone, glycolic acid-lactic acid copolymer, glycolic acid-caprolactone copolymer, lactic acid-caprolactone copolymer, poly(p-dioxanone), collagen, denatured collagen, gelatin, chitin, and chitosan.

4. A process for producing an artificial heart valve, comprising:
   forming at least one sinus of Valsalva which is bioabsorbable on a base body; and
   attaching at least one valve cusp which is bioabsorbable to the base body,
   wherein at least one of the sinus or the cusp is made by a method comprising: setting a fibrous reinforcement structure made of a bioabsorbable polymer in a mold; pouring a bioabsorbable polymer material into the mold; freezing the bioabsorbable polymer material; and lyophilizing the bioabsorbable polymer material.

5. The process according to claim 4, wherein the attaching of the valve cusp comprises conducting by adhesion.

6. The process according to claim 4, wherein the attaching of the valve cusp comprises conducting by suture.

7. The process according to claim 6, wherein the suture is conducted using a bioabsorbable suture.

8. The process according to claim 4, wherein the attaching of the valve cusp comprises conducting by thermal fusion.

9. The process according to claim 4, wherein the attaching of the valve cusp comprises using a bioabsorbable polymer solution.

10. The process according to claim 4, wherein the base body having the sinus of Valsalva is formed to be tubular by molding and one end of a substrate is folded and subjected to heat set so as to form the valve cusp.

11. The process according to claim 4, wherein the bioabsorbable material is selected from the group consisting of polyglycolic acid, polylactic acid, polycaprolactone, glycolic acid-lactic acid copolymer, glycolic acid-caprolactone copolymer, lactic acid-caprolactone copolymer, poly(p-dioxanone), collagen, denatured collagen, gelatin, chitin, and chitosan.

* * * * *